United States Patent [19]
Shiraiwa et al.

[11] Patent Number: 6,020,531
[45] Date of Patent: Feb. 1, 2000

[54] PROCESS FOR THE PREPARATION OF 2,6-DISUBSTITUTED BENZOTHIOPHENE COMPOUNDS

[75] Inventors: Masafumi Shiraiwa, Yokohama; Shuichiro Sato; Koji Doguchi, both of Kawasaki, all of Japan

[73] Assignee: Teikoku Hormone Mfg. Co., Ltd., Tokyo, Japan

[21] Appl. No.: 09/230,279

[22] PCT Filed: Jul. 15, 1997

[86] PCT No.: PCT/JP97/02440

§ 371 Date: Jan. 25, 1999

§ 102(e) Date: Jan. 25, 1999

[87] PCT Pub. No.: WO98/03501

PCT Pub. Date: Jan. 29, 1998

[30] Foreign Application Priority Data

Jul. 24, 1996 [JP] Japan .................................. 8-212200

[51] Int. Cl.[7] .......................... C07C 47/52; C07C 45/00; C07D 333/52; C07D 333/56
[52] U.S. Cl. ........................... 568/425; 568/433; 549/49; 549/51; 549/57
[58] Field of Search ................. 549/49, 51, 57; 568/433, 425

[56] References Cited

U.S. PATENT DOCUMENTS

| | | | |
|---|---|---|---|
| 2,949,471 | 8/1960 | Prey | 260/330.5 |
| 5,169,961 | 12/1992 | Dickman et al. | 549/57 |
| 5,266,705 | 11/1993 | Yazawa et al. | 549/57 |
| 5,292,894 | 3/1994 | Ebel et al. | 549/43 |
| 5,298,630 | 3/1994 | Kagano et al. | 549/57 |
| 5,472,962 | 12/1995 | Koizumi et al. | 514/233.5 |
| 5,606,075 | 2/1997 | Hoard et al. | 549/49 |
| 5,710,285 | 1/1998 | Hauser et al. | 549/4 |
| 5,908,859 | 6/1999 | Cullinan et al. | 514/443 |

FOREIGN PATENT DOCUMENTS

| | | |
|---|---|---|
| 0641791 | 3/1995 | European Pat. Off. . |
| 5-140148 | 6/1993 | Japan . |
| WO 93/10113 | 5/1993 | WIPO . |
| 94/27985 | 12/1994 | WIPO . |

OTHER PUBLICATIONS

Chemical Abstracts, vol. 55, no. 15, Jul. 24, 1961 (1961-07-24), Columbus, Ohio, US; Pailer et al.: "Synthesis and paper chromatographic estimation of methyl-and ethylthianaphthenes", column 14422c; XP002109156 & Monatsh. Chem. (1960) 91, 1070–1076.

Effenberger et al.: "Darstellung und Reaktionen von Sulfensäure–trifluormethan–sulfonsäure–anhydriden", Chem. Ber., vol. 115, no. 12. 1982, pp. 3719–3736, XP002109154.

Descamps, et al., "Recharges dans la serie des benzo(b)thiopenes. II. Acides benzo(b)thienyl–2 ou –3 acetiques, agents, anti–inflammatoires potentiels", Chum. Ther., vol. 8, No. 5 (1973), pp. 536–544.

DeGroot, "A novel synthesis of 1–benzothiophenes from 2–(phynylthio)–aldehydes.", Synthesis, No. 4 (1985), pp. 434–436.

Graham et al., "Topically Active Carbonic Anhydrase Inhibitors. 2. Benzo[b]thiophenesulfonamide Derivatives with Ocular Hypotensive Activity", J. Med. Chem. 1989, 32, 2548–2554.

*Primary Examiner*—Deborah C. Lambkin
*Attorney, Agent, or Firm*—Wenderoth, Lind & Ponack, L.L.P.

[57] ABSTRACT

A benzothiophene compound represented by a formula:

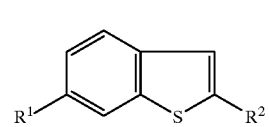

(I)

wherein $R^1$ represents a lower alkyl group, and $R^2$ represents a halogen atom; a lower alkyl group; or a cycloalkyl group or cycloalkenyl group which may optionally be substituted with a lower alkyl group, a hydroxy group, an acyloxy group or an oxo group, which is a useful intermediate for synthesizing a 2-substituted-3-(4-substituted benzoyl)-6-hydroxybenzo[b]-thiophene derivative having an antiestrogenic activity can be produced in an industrially advantageous manner by subjecting a compound represented by a formula:

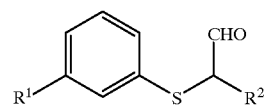

(II)

to a ring-closing reaction. Further, the novel compound of the formula (II) described above is a useful intermediate in the process of the present invention.

7 Claims, No Drawings

PROCESS FOR THE PREPARATION OF 2,6-DISUBSTITUTED BENZOTHIOPHENE COMPOUNDS

This application is a 371 of PCT/JP97/02 440 Jul. 15, 1997.

FIELD OF THE INVENTION

The present invention relates to a novel production process of a benzothiophene compound which is a useful intermediate for synthesizing some kind of a 2-substituted-3-(4-substituted benzoyl)-6-hydroxybenzo-[b]thiophene derivative having an antiestrogenic activity, and an intermediate compound useful in the production process.

DESCRIPTION OF THE RELATED ART

Disclosed as a 2-substituted-3-(4-substituted benzoyl)-6-hydroxybenzo[b]thiophene derivative having an antiestrogenic activity in a WO93/10113 pamphlet (=U.S. Pat. No. 5472962, EP-A-641791) is a group of compounds represented by the following formula (A):

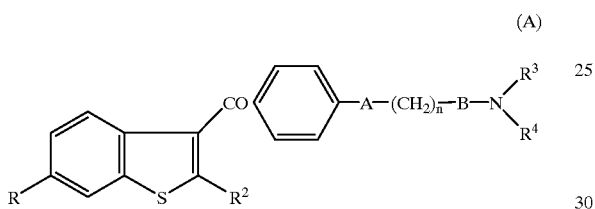

wherein:
R represents a hydrogen atom, a hydroxy group, a lower alkoxy group, an acyloxy group or an N,N-di-lower alkyl substituted or unsubstituted carbamoyloxy group,
$R^2$ represents a halogen atom; a lower alkyl group; or a cycloalkyl group or cycloalkenyl group which may optionally be substituted with a lower alkyl group, a hydroxy group, an acyloxy group or an oxo group,
$R^3$ and R4 each represent a hydrogen atom or a lower alkyl group or represent a heterocyclic group which may further contain a hetero atom selected from O, S and N together with a nitrogen atom to which they are bonded,
A represents O or $CH_2$,
B represents C=O or $CH_2$, and
n represents 1 or 2.

It is disclosed in the WO pamphlet described above that a benzothiophene compound represented by the following formula:

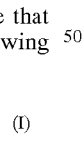

wherein $R^1$ represents a lower alkyl group, and $R^2$ represents a halogen atom; a lower alkyl group; or a cycloalkyl group or cycloalkenyl group which may optionally be substituted with a lower alkyl group, a hydroxy group, an acyloxy group or an oxo group,
is an important synthetic intermediate for the compound represented by the formula (A) described above. In the above WO pamphlet, the compound represented by the formula (I) described above is synthesized according to the following reaction formula 1 with 6-alkoxybenzo[b]-thiophene (a compound represented by the following formula (B)) being used as a starting material:

Reaction formula 1

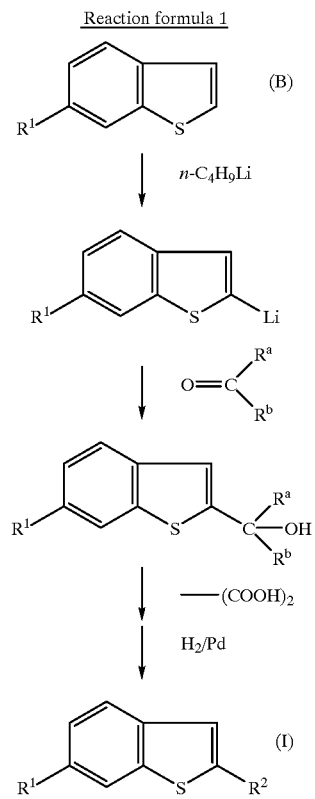

In the respective formulae described above, $R^a$ and $R^b$ each represent a lower alkyl group or represent a cycloalkyl group which may optionally be substituted with a lower alkyl group or an oxo group, together with a carbon atom to which they are bonded, and $R^1$ and $R^2$ have the same meanings as described above.

On the other hand, nothing on a synthetic process of the compound represented by the formula (B) described above which is a starting material in the reaction formula 1 described above is described in the above WO pamphlet. However, a process shown by the following reaction formula 2 described in J. Med. Chem., vol. 32, pp. 2548 to 2554 (1989) is known as a process for synthesizing the compound represented by the formula (B) described above in which $R^1$ represents, for example, methoxy, that is, a compound represented by the following formula (B-1):

Reaction formula 2

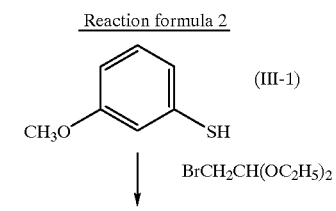

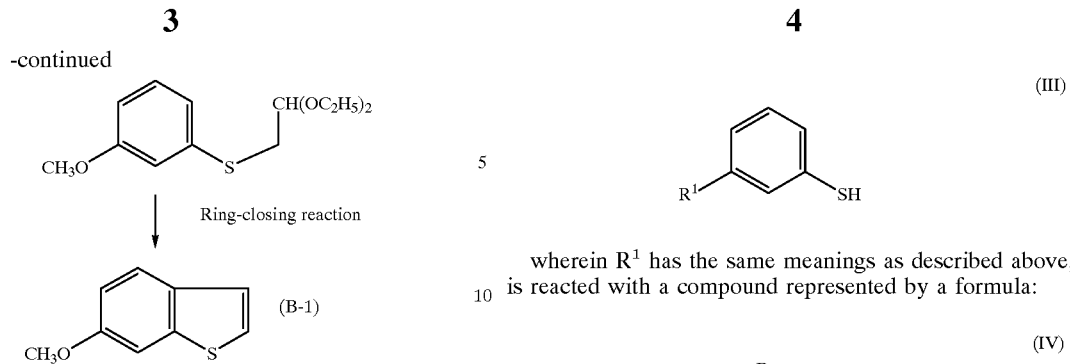

However, the yield of a ring-closing reaction in the reaction formula 2 described above is about 60%, and the regioselectivity is about 10:1. In addition, in a reaction (reaction in the reaction formula 1 described above) for introducing a substituent into the 2 position of the benzothiophene, butyl lithium which is not industrial is used as a reaction reagent, and it can never be said that a hydrogenation reaction following it is an industrially advantageous reaction.

The present inventors have continued various researches on a production process of the benzothiophene compound represented by the formula (I) described above, and as a result thereof, they have found a production process in which the benzothiophene compound represented by the formula (I) can be produced only at two steps with 3-alkoxythiophenol being used as a starting material using industrially advantageous reaction reagent and reaction conditions and which is excellent in a yield and a regioselectivity.

DISCLOSURE OF THE INVENTION

According to the present invention, provided is a production process of the benzothiophene compound represented by the formula:

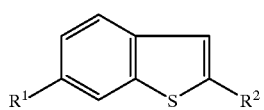 (I)

wherein $R^1$ and $R^2$ have the same meanings as described above, characterized by that a compound represented by a formula:

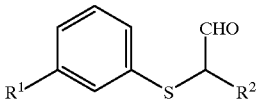 (II)

wherein $R^1$ and $R^2$ have the same meanings as described above, is subjected to a ring-closing reaction.

Also, according to the present invention, provided is a production process of the compound represented by the formula (II) described above, characterized by that 3-alkoxythiophenol represented by a formula:

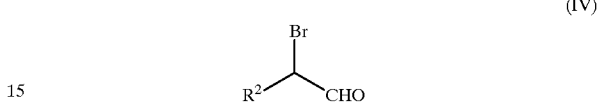 (III)

wherein $R^1$ has the same meanings as described above, is reacted with a compound represented by a formula:

(IV)

wherein $R^2$ has the same meanings as described above.

Further, according to the present invention, provided is the compound represented by the formula (II) described above which is an advantageous intermediate in the production process of the present invention.

The term [lower] in the present specification means that a group or compound to which this term is given has 6 or less carbon atoms, preferably 4 or less carbon atoms.

In the formula (I) described above, the [lower alkyl group] can be linear or branched and includes, for example, methyl, ethyl, n-propyl, isopropyl, n-butyl, isobutyl, sec-butyl, tert-butyl, sec-pentyl and 1-ethylpropyl groups. The [lower alkoxy group] is a lower alkyloxy group in which an alkyl part has the same meanings as described above and includes, for example, methoxy, ethoxy, n-propoxy, isopropoxy and n-butoxy groups. Also, the [cycloalkyl group] can have 3 to 12 carbon atoms, preferably 3 to 8 carbon atoms and includes, for example, cyclopropyl, cyclobutyl, cyclopentyl, cyclohexyl, cycloheptyl and cyclooctyl groups. The [cycloalkenyl group] can have 4 to 12 carbon atoms, preferably 5 to 8 carbon atoms and includes, for example, 1-cyclopentenyl, 1-cyclohexenyl, 1-cycloheptenyl and 1-cyclooctenyl groups. Further, a fluorine, chlorine or bromine atom is included in the [halogen atom].

To be specific, the [acyloxy group] is a group represented by a formula $R^5CO—O—$, wherein $R^5$ represents a hydrogen atom; a lower alkyl group which may optionally be substituted with a halogen atom, an amino group, a carbonyl group, a lower alkoxycarbonyl group, a lower alkanoyloxy group, a carbamoyl group or an aryl group; a lower alkenyl group which may be substituted with an aryl group; a lower cycloalkyl group; or an aryl group which may optionally be substituted with a lower alkyl group, a lower alkoxy group or a halogen atom. Also, examples of the [acyloxy group] include acetoxy, propionyloxy, trifluoroacetyloxy, glycyloxy, 3-carboxypropionyloxy, 3-ethoxycarbonylpropionyloxy, acetoxyacetoxy, phenylacetoxy, acryloyloxy, cyclohexanecarbonyloxy, benzoyloxy, 4-methoxybenzoyloxy and 2-chlorobenzoyloxy groups.

On the other hand, when $R^2$ represents [a cycloalkyl group or cycloalkenyl group which may optionally be substituted with a lower alkyl group, a hydroxy group, an acyloxy group or an oxo group], the above cycloalkyl group or cycloalkenyl group can be unsubstituted or substituted with one group selected from a lower alkyl group, a hydroxy group, an acyloxy group and an oxo group. The cycloalkyl group or cycloalkenyl group thus substituted includes, for example, 3-methylcyclopentyl, 3-hydroxycyclopentyl, 2-methylcyclohexyl, 3-methylcyclohexyl, 4-methylcyclohexyl, 4-hydroxycyclohexyl, 4-acetoxycyclohexyl, 4-benzoyloxycyclohexyl, 4-oxocyclohexyl and 2-methylcycloheptyl groups.

In the production process of the compound represented by the formula (I) described above according to the present invention, the preferred compounds represented by the formulas (I) and (II) described above are the compounds in which $R^2$ represents a branched lower alkyl group or a cycloalkyl group having 3 to 8 carbon atoms which may optionally be substituted with a lower alkyl group or a hydroxy group. Among them, the compounds represented by the formulas (I) and (II) described above in which $R^2$ represents cyclohexyl are particularly suitable.

According to the present invention, the compound represented by the formula (I) described above is produced by subjecting the compound represented by the formula (II) described above to a ring-closing reaction.

Usually, the ring-closing reaction can be carried out in an inert organic solvent including halogenated hydrocarbons such as methylene chloride and chloroform; aromatic hydrocarbons such as benzene, toluene, xylene and chlorobenzene; alkanes such as petroleum ether and hexane; and nitro hydrocarbons such as nitrobenzene and nitromethane under the presence of acids, for example, Lewis acids such as aluminum chloride, aluminum bromide, zinc chloride, boron trifluoride, titanium tetrachloride and stannic chloride, or strong acids such as sulfuric acid and p-toluenesulfonic acid. In general, the reaction temperature is suitably a temperature of from cooling with ice to a reflux temperature of the reaction mixture, preferably a temperature of from cooling with ice to about 100° C.

In the reaction described above, the use amount of the acids based on the compound of the formula (II) is a catalytic amount. To be specific, it is advantageous to use the acids usually in a proportion of an extent of 0.1 to 10 moles, preferably an extent of 0.5 to 5 moles per mole of the compound of the formula (II). Thus, the benzothiophene compound of the formula (I) described above is produced in a high yield.

In the present ring-closing reaction, a 2,4-disubstituted benzothiophene compound as a by-product is formed as well in addition to the compound of the formula (I) which is a principal product. However, the present reaction is a reaction having a very high regioselectivity, and in the case of the ring-closing reaction when the compound of the formula (II) described above is, for example, 2-(3-methoxyphenylthio) cyclohexylacetaldehyde, a result showing such very high regioselectivity that the ratio of the principal product to the by-product is about 30:1.

The benzothiophene compound of the formula (I) described above thus obtained can be isolated from the reaction mixture and purified by conventional methods, for example, methods such as extraction, filtration, distillation, recrystallization, column chromatography and thin layer chromatography.

The compound of the formula (II) which is used as a starting material in the reaction described above is a novel compound which have not hitherto been described in the literatures, and it is an important intermediate when the process of the present invention is carried out.

The compound of the formula (II) described above which is used as a starting material in the process of the present invention can be prepared, for example, by reacting the compound of the formula (III) described above with the compound of the formula (IV) described above.

Usually, the above reaction can be carried out in an inert solvent including ketones such as acetone and methyl ethyl ketone; ethers such as tetrahydrofuran and dioxane; nitriles such as acetonitrile; halogenated hydrocarbons such as methylene chloride and chloroform; and aromatic hydrocarbons such as benzene and toluene under the presence of bases, for example, inorganic bases such as potassium carbonate, sodium carbonate, sodium hydroxide and potassium hydroxide or organic bases such as triethylamine, diisopropylethylamine and pyridine. Further, addition of a reducing agent such as triphenylphosphine and tributylphosphine in this reaction can more effectively inhibit a side reaction. In general, the reaction temperature is suitably a temperature of from cooling with ice to about 100° C., preferably a temperature of from cooling with ice to about room temperature.

In the reaction described above, the compound of the formula (IV) is advantageously used usually in a proportion of at least one mole, preferably an extent of 1.05 to 1.5 mole per mole of the compound of the formula (III). Also, the base described above is suitably added generally in a proportion of at least one mole, preferably a level of 1.05 to 2 moles per mole of the compound of the formula (III). The use amount of the reducing agent described above shall not specifically be restricted and is advantageously used in a proportion of a level of 0.1 to 0.5 mole per mole of the compound of the formula (IV). Thus, the compound of the formula (II) described above can be obtained in a high yield.

The benzophenone compound of the formula (I) described above which is produced by the process of the present invention described above provides the compound of the formula (A) described above having an excellent antiestrogenic activity, and being effective for therapy of endometriosis, uterine adenomyosis, endometrial cancer, breast cancer and osteoporosis, for example, by acylating with a compound of a formula:

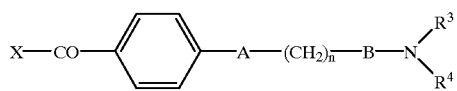

wherein $R^3$, $R^4$, A, B and n have the same meanings as described above, and X is a halogen atom, and converting the group $R^1$ in the resulting compound, if necessary, to a hydroxy group, acyloxy group or N,N-di-lower alkyl group-substituted or unsubstituted carbamoyloxy group according to the method described in the WO93/10113 described above.

EXAMPLES

The present invention shall be explained below in further detail with reference to examples.

Example 1

(a) The mixed solution of a 15% sodium hypochlorite aqueous solution 540 ml and a saturated sodium hydrogencarbonate aqueous solution 540 ml was dropwise added to a methylene chloride solution of 500 ml containing cyclohexylethanol 128 g and 2,2,6,6-tetramethyl-piperidine-1-oxyl 500 mg at 25° C. or lower and stirred for 30 minutes. A 20% sodium thiosulfate aqueous solution 150 ml was added and shaken, and then the aqueous layer is separated from the organic layer and further extracted twice with methylene chloride 200 ml. The organic layers are put together and washed once with a 10% sodium thiosulfate aqueous solution 150 ml, twice with 10% hydrochloric acid 200 ml, twice with a satrated sodium hydrogencarbonate aqueous solution 200 ml and once with saturated brine 200 ml in order. After drying on sodium sulfate anhydrous, the solvent is distilled off under reduced pressure, and the residue is distilled under reduced pressure, whereby a pale yellow liquid of cyclohexylacetaldehyde 98.5 g is obtained. The yield: 78% bp: 50 to 55° C./7 mmHg $^1$H-NMR (CDCl$_3$, δ): 0.7 to 2.5 (13H, m), 9.75 (1H, t, J=2.4 Hz) MS (m/z): 125 (M$^+$–1)

(b) Bromine 47.5 ml is dropwise added to ethyl ether containing cyclohexylacetaldehyde 112 g at 10° C. or lower, and stirring is carried out at a room temperature for 2 hours. Ice 50 g and a 20% sodium thiosulfate aqueous solution 50 ml are added and shaken. Then, the organic layer is separated and washed with a 10% sodium thiosulfate aqueous solution 100 ml. The aqueous layers are put together and extracted with ethyl ether 100 ml, and the organic layers are put together and washed twice with saturated sodium hydrogencarbonate 70 ml and once with saturated brine 70 ml. After drying on magnesium sulfate anhydrous, the solvent is distilled off under reduced pressure, and the residue is distilled under reduced pressure, whereby a pale yellow liquid of 2-bromocyclohexylacetaldehyde 154 g is obtained. The Field: 86% bp: 81 to 86° C./4 mmHg $^1$H-NMR (CDCI$_3$, δ): 0.7 to 2.4 (11H, m), 4.00 (1H, dd, J=4.4 Hz), 9.50 (1H, d, J=4.4 Hz)

(c) The mixture of 2-bromocyclohexylacetaldehyde 1.14 g, 3-methoxythiophenol 779 mg, potassium carbonate 1.54 g and acetone 20 ml is stirred at a room temperature for 21 hours. The solvent is distilled off under reduced pressure, and water 10 ml is added. Then, extraction is carried out twice with ethyl ether 20 ml. The organic layer is washed with saturated brine 5 ml and then dried on magnesium sulfate anhydrous. The solvent is distilled off under reduced pressure, and the residue is subjected to silica gel chromatography (hexane: chloroform=9:1), whereby colorless oily 2-(3-methoxyphenylthio)cyclohexylacetaldehyde 1.26 g is obtained. The yield: 86%.

$^1$H-NMR (CDCI$_3$,δ): 0.8 to 2.2 (11H, m), 3.2 to 3.6 (1H, m), 3.80 (3H, s), 6.5 to 7.7 (4H, m), 9.50 (1H, d, J=5.3 Hz) MS (m/z): 264 (M$^+$)

(d) A methylene chloride solution 12 ml containing 2-(3-methoxyphenylthio)cyclohexylacetaldehyde 200 mg is dropwise added to a methylene chloride solution 12 ml containing boron trifluoride-ethyl ether 0.093 ml at a room temperature, and stirring is carried out for 2 hours. A sodium hydroxide aqueous solution 10 ml is added and stirred at a room temperature for one hour. Then, the solution is shaken, and the organic layer is separated and washed with saturated brine 5 ml. After drying on magnesium sulfate anhydrous, the solvent is distilled off under reduced pressure, and the residue is subjected to silica gel chromatography (hexane : chloroform=5:1), whereby colorless solid 2-cyclo-hexyl-6-methoxybenzo[b]thiophene 162 mg is obtained from the second elution fraction. The yield: 87%.

$^1$H-NMR (CDCI$_3$, δ): 1.2 to 3.0 (11 H, m), 3.84 (3H, s), 6.8 to 7.3 (3H, m), 7.50 (11H, d, J=8.6 Hz) MS (m/z): 246 (M$^+$–1)

Colorless oily 2-cyclohexyl-4-methoxybenzo-[b]thiophene 6 mg (yield: 2.4%) which is a by-product is obtained from the first elution fraction.

$^1$H-NMR (CDCI$_3$δ): 1.1 to 3.0 (11H, m), 3.93 (3H, s), 6.6 to 7.4 (3H, m) MS (m/z): 246 (M$^+$)

Example 2

(a) Triethylamine 481 ml is added to the mixture of 3-methoxythiophenol 322.5 g, triphenylphosphine 241.3 g, water 204 ml and tetrahydrofuran 2.3 liter under nitrogen atmosphere while cooling with ice under stirring, and then 2-bromocyclohexylacetaldehyde 518.9 g is dropwise added. Stirring is carried out at a room temperature for one hour, and then stirring is further continued at 60° C. for 2.5 hours. Water 200 ml is added, and the mixture is shaken. The organic layer is separated and washed twice with 10% hydrochloric acid 500 ml and twice with saturated brine 400 ml, and then it is dried on magnesium sulfate anhydrous. The solvent is distilled off under reduced pressure, and the residue is dissolved in hexane 2 liter and stirred at a room temperature for 13 hours. After cooling with ice, deposited crystals are filtered off, and the solvent is distilled off under reduced pressure, whereby yellow oily 2-(3-methoxyphenylthio)cyclohexylacetaldehyde 820.3 g is obtained.

(b) 2-(3-Methoxyphenylthio)cyclohexylacetaldehyde 408 g obtained at the step (a) described above is dropwise added to a toluene solution 1.5 liter containing boron trifluoride-ethyl ether 171 ml in 4 hours while cooling with ice, and stirring is continued for further 30 minutes. A 2N sodium hydroxide aqueous solution 4 liter is added, and stirring is continued for 14 hours. Then, the organic layer is washed with saturated brine 1 liter. After drying on magnesium sulfate anhydrous, the solvent is distilled off under reduced pressure. Acetone 1.3 liter is added, and 30% hydrogen peroxide 100 ml is dropwise added. Then, a 10% sodium thiosulfate aqueous solution 1 liter and methanol 1.3 liter are added and stirred for 17 hours. Deposited crystals are filtered and washed with methanol, whereby white crystal of 2-cyclohexyl-6-methoxybenzo[b]thiophene 438 g is obtained.

Aggregate yield from the step (a): 78%.

We claim:

1. A production process of a benzothiophene compound represented by a formula:

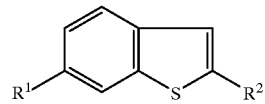

(I)

wherein R$^1$ represents a lower alkyl group, and R$^2$ represents a halogen atom; a lower alkyl group; or a cycloalkyl group or cycloalkenyl group which may optionally be substituted with a lower alkyl group, a hydroxy group, an acyloxy group or an oxo group, characterized by that a compound represented by a formula:

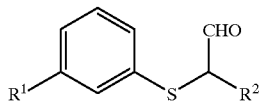

(II)

wherein R$^1$ and R2 have the same meanings as described above, is subjected to a ring-closing reaction.

2. The production process of a benzothiophene compound as described in claim 1, wherein R$^2$ represents a lower alkyl group or a cycloalkyl group having 3 to 8 carbon atoms, which may optionally be substituted with a lower alkyl group or a hydroxy group.

3. The production process of a benzothiophene compound as described in claim 1, wherein R$^2$ represents a cyclohexyl group.

4. A production process of the compound of the formula (II) as described in claim 1, characterized by that a compound represented by a formula:

(III)

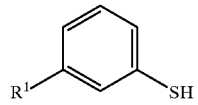

wherein $R^1$ has the same meanings as described in claim 1
is reacted with a compound represented by a formula:

(IV)

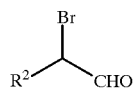

wherein $R^1$ has the same meanings as described in claim 1.

5. A compound represented by a formula:

(II)

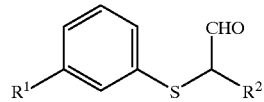

wherein $R^1$ and $R^2$ have the same meanings as described in claim 1.

6. The compound as described in claim 5, wherein $R^2$ represents a lower alkyl group or a cycloalkyl group having 3 to 8 carbon atoms, which may optionally be substituted with a lower alkyl group or a hydroxy group.

7. The compound as described in claim 5, wherein $R^2$ represents a cyclohexyl group.

* * * * *